United States Patent [19]

Shioyama

[11] 4,226,809
[45] Oct. 7, 1980

[54] HYDROGENATION OF UNSATURATED DINITRILES USING CATALYST COMPRISING REACTION PRODUCTS OF NICKEL COMPOUND AND OF A PALLADIUM COMPOUND EACH WITH AN ALKALI METAL BOROHYDRIDE

[75] Inventor: Tod K. Shioyama, Bartlesville, Okla.

[73] Assignee: Phillips Petroleum Company, Bartlesville, Okla.

[21] Appl. No.: 64,470

[22] Filed: Aug. 7, 1979

[51] Int. Cl.$^2$ .............................................. C07C 85/12
[52] U.S. Cl. ................................ 260/583 P; 252/432; 260/690
[58] Field of Search ...................... 260/583 K, 583 P; 252/432

[56] References Cited

U.S. PATENT DOCUMENTS

| 2,690,456 | 9/1954 | Renfrew et al. | 260/583 K |
| 2,748,108 | 5/1956 | Paul et al. | 252/432 X |
| 2,784,232 | 3/1957 | Terry et al. | 260/583 K |
| 2,856,428 | 10/1958 | Brown | 260/570.9 |
| 3,294,853 | 12/1966 | Arrigo | 252/432 X |
| 3,880,929 | 4/1975 | Drake | 260/583 P |
| 3,891,707 | 6/1975 | Waddan | 260/583 K |
| 4,078,002 | 3/1978 | Brown | 260/583 K |

FOREIGN PATENT DOCUMENTS

| 746669 | 2/1970 | France | 260/583 K |
| 40-13842 | 2/1965 | Japan | 260/583 K |

OTHER PUBLICATIONS

Polkovnikov et al., "Chem. Ab.", vol. 54, Ab. No. 1264$^2$, (1960).

*Primary Examiner*—John Doll

[57] ABSTRACT

A branched chain unsaturated aliphatic dinitrile, e.g., as contained in a reaction product of acrylonitrile with isobutylene is subjected to hydrogenation under hydrogenation conditions in the presence of a combination or composition of catalysts including essentially at least one component selected from the group consisting of reaction products of an alkali metal borohydride with a palladium compound which is reducible by hydrogen to the elemental form and another component selected from a group consisting of the reaction products of an alkali metal borohydride with a nickel compound which is reducible by hydrogen to the elemental form, the individual components being primarily active as follows: the nickel component to hydrogenate nitrile groups and the palladium component to hydrogenate the olefinic unsaturation in the particular compounds hydrogenated; the process being carried out as a one-step process when the components are in admixture and as a two-step process when the components are used separately, one of them in one step and the other in another step of a two-step process. Completely saturated branched aliphatic diamines are produced.

20 Claims, No Drawings

HYDROGENATION OF UNSATURATED DINITRILES USING CATALYST COMPRISING REACTION PRODUCTS OF NICKEL COMPOUND AND OF A PALLADIUM COMPOUND EACH WITH AN ALKALI METAL BOROHYDRIDE

BRIEF SUMMARY OF THE INVENTION

Branched, unsaturated aliphatic dinitrile is hydrogenated to produce branched, saturated aliphatic diamine employing a catalytic material comprising a reaction product of a nickel compound with an alkali metal borohydride and a reaction product of a palladium compound with an alkali metal borohydride.

The catalyst components are, broadly speaking, separately prepared and subsequently brought together, as on a carrier, for use in the hydrogenation which can be a one-step process when the mixture of catalytic components is used and which is a two-step process when each catalyst component is separately used, each of them only in one step of the two step process. The two catalysts are required to obtain substantially complete hydrogenation of the branched-chain, unsaturated aliphatic dinitrile.

DETAILED DESCRIPTION

In one of its aspects, this invention relates to a process for the hydrogenation of a branched, unsaturated aliphatic dinitrile. In another of its aspects, the invention relates to a process for the preparation of branched, saturated aliphatic diamine. In a further aspect of the invention, relates to the catalytic hydrogenation of a branched, unsaturated aliphatic dinitrile. In a further aspect of the invention, it relates to a catalyst composition. In a still further aspect of the invention it relates to a hydrogenation process employing a combination of at least two catalysts together or separately.

In one of its concepts, the invention provides a process for the hydrogenation of a branched, unsaturated aliphatic dinitrile in the presence of catalytic material including a reaction product of a nickel compound with an alkali metal borohydride and a reaction product of a palladium compound with an alkali metal borohydride. In another of its concepts, the invention provides a one-step hydrogenation process using a mixture of the recited catalyst components. In another of its concepts, the invention provides a two-step process in which each of the catalyst components is employed in a separate step of the process. In a further concept of the invention, there is provided a process for the preparation of branched, saturated aliphatic diamine by catalytic hydrogenation, as herein described, in the presence of a catalyst comprising essentially a reaction product of a nickel compound with an alkali metal borohydride and a reaction products of a palladium compound with an alkali metal borohydride. Further, still, a concept of the invention provides a process, as herein described, involving two steps in step one of which one of the catalyst components or reaction product is employed while in the other step of which another of the components of the catalytic combination is used.

Various processes for the catalytic hydrogenation of unsaturated aliphatic dinitriles to saturated aliphatic diamines are known to the art. Group VIII metal catalysts such as cobalt, nickel, ruthenium, rhodium, or palladium have been employed as catalysts for the hydrogenation of various feedstocks in these processes. However, it has been discovered that many of these hydrogenation catalyst materials are not always efficient or effective for the hydrogenation of certain unsaturated aliphatic dinitriles having the formula

wherein each R is an alkylene or an alkylidene radical, and each R' is an alkyl radical.

I have now found that branched-chain unsaturated aliphatic dinitriles having the formula just given can be efficiently reduced to branched-chain saturated aliphatic diamines using a catalyst essentially comprising a component selected from a group consisting of the reaction products of an alkali metal borohydride with a palladium compound which is reducible by hydrogen to the elemental form and mixtures thereof, and another component selected from a group consisting of the reaction products of an alkali metal borohydride with a nickel compound which is reducible by hydrogen to the elemental form as in the presence of diluent, ammonia and hydrogen and, optionally, and now preferably, in the presence of a solid support.

I have further found, as the data herein illustrate, that the components of the catalyst should be prepared separately, and not in the presence of each other, and then subsequently mixed together for use in the one-step hydrogenation process, herein described.

It is an object of this invention to provide a process for the catalytic hydrogenation of a branched, unsaturated aliphatic dinitrile. It is another object of this invention to provide a catalytic combination or mixture for use in hydrogenation of a dinitrile and/or an unsaturated dinitrile. It is a further object of this invention to provide a process for the preparation of a branched, saturated aliphatic diamine by catalytic hydrogenation of a branched, unsaturated aliphatic dinitrile. It is a further object of the invention to provide a catalytic combination or mixture of components for use in a process for the catalytic hydrogenation of a dinitrile and/or an unsaturated compound e.g., a branched, unsaturated aliphatic dinitrile. It is a further object of the invention to provide a one-step process for the hydrogenation of a branched, unsaturated aliphatic dinitrile. It is a further object of the invention, still, to provide a two-step hydrogenation process effected for the substantially complete hydrogenation of a branched, unsaturated aliphatic dinitrile.

Other aspects, concepts, objects and the several advantages of the invention are apparent from a study of this disclosure and the appended claims.

According to the present invention, a branched-chain unsaturated aliphatic dinitrile is hydrogenated or reduced to a branched-chain saturated aliphatic diamine using a catalyst essentially comprising a mixture or a combination of at least two components: a reaction product of an alkali metal borohydride with a palladium compound which is reducible by hydrogen to the elemental form, and mixtures thereof, and a reaction product of an alkali metal borohydride with a nickel compound which is reducible by hydrogen to the elemental form as in the presence of a diluent, ammonia and hydrogen and, optionally and now preferably, in the presence of a solid support, e.g. alumina.

The branched-chain unsaturated aliphatic dinitriles which are advantageously and efficiently hydrogenated in accordance with the process of this invention are the unsaturated dinitriles of the formula:

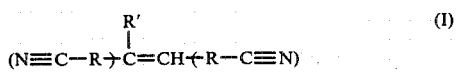
(I)

wherein each R is independently selected from the group consisting of an alkylene radical and an alkylidene radical, and R' is an alkyl radical. Each R will generally have from one to fifteen carbon atoms, preferably from one to six, and more preferably from one to three carbon atoms. In general, the unsaturated dinitrile reactant of formula (I) will contain from seven to 30 carbon atoms, preferably from eight to 16 carbon atoms, and more preferably from nine to 12 carbon atoms. R' will generally have one to six carbon atoms.

Representative of unsaturated reactant species of formula (I) include such compounds as
4-methyl-3-hexenedinitrile,
4-ethyl-3-hexenedinitrile,
5-methyl-4-nonenedinitrile,
5-ethyl-4-decenedinitrile,
7-methyl-6-tridecenedinitrile,
7-methyl-6-pentadecenedinitrile,
12-methyl-12-tetracosenedinitrile,
10-hexyl-9-tetracosenedinitrile,
2,3-dimethyl-3-hexenedinitrile,
2,4,6-trimethyl-3-heptenedinitrile,
4-ethyl-6,7-dimethyl-3-octenedinitrile,
2,4,6-triethyl-3-octenedinitrile,
2-ethyl-4,6-dipropyl-3-octenedinitrile,
2-methyl-4,6,8,10-tetrapropyl-3-dodecenedinitrile,
2,4,7,9,11,13,15-heptaethyl-6-hexadecenedinitrile,
and mixtures thereof.

If desired, other unsaturated dinitrile reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula:

(II)

wherein each R" is independently selected from the group consisting of an alkylene radical and an alkylidene radical. In general, each R" will have from one to 15 carbon atoms, preferably from one to seven carbon atoms, and more preferably from one to four carbon atoms. The dinitriles of formula (II) will generally contain from six to 30 carbon atoms, preferably from eight to 16 carbon atoms, and more preferably from nine to 12 carbon atoms. Representative unsaturated dinitrile reactants of formula (II) include such compounds as
3-methylenehexanedinitrile,
4-methyleneheptanedinitrile,
5-methylenenonanedinitrile,
6-methyleneundecanedinitrile,
7-methylenetridecanedinitrile,
8-methylenepentadecanedinitrile,
12-methylenetetracosanedinitrile,
15-methylenenonacosanedinitrile,
2-methyl-3-methylenepentanedinitrile,
2,4-dimethyl-3-methylenepentanedinitrile,
2-methyl-4-methyleneoctanedinitrile,
2-methyl-7-ethyl-4-methyleneoctanedinitrile,
2,4,8-trimethyl-6-methylenedodecanedinitrile,
2,4,8,10-tetrapropyl-6-methylenedodecanedinitrile,
2,26-dimethyl-14-methyleneheptacosanedinitrile,
and mixtures thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the invention increase with increasing concentrations of the dinitriles of formula (I) in the feedstock. Thus, the process of the invention is even more advantageous for concentrations of the dinitriles of formula (I) in the feedstock of at least 5 weight percent. The invention is considered to be particularly advantageous for dinitrile feedstocks having a concentration of the dinitriles of formula (I) of at least 10 weight percent.

A presently preferred branched-chain unsaturated aliphatic dinitrile feedstock for employment in the practice of this invention is the dinitrile reaction product mixture obtained by the reaction of isobutylene and acrylonitrile. This dinitrile reaction product mixture generally comprises
5-methyl-4-nonenedinitrile,
2,4-dimethyl-4-octenedinitrile,
2,4-dimethyl-3-octenedinitrile,
2,4,6-trimethyl-3-heptenedinitrile,
5-methylenenonanedinitrile,
2-methyl-4-methyleneoctanedinitrile, and
2,6-dimethyl-4-methyleneheptanedinitrile.
The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

One skilled in the art in possession of this disclosure, having studied the same, can readily determine by mere routine tests what will be optimum under all other circumstances for the particular hydrogenation of the invention which he seeks to perform. Accordingly, the foregoing and following information, herein given, are given to comply as fully as possible with the statutes and rules and practice thereunder without, however, in any way seeking to unduly limit the scope of the claimed invention.

In the practice of this invention, the catalytic hydrogenation of the unsaturated dinitrile reactant of formula (I) results primarily in the formation of saturated diamine reaction products having the formula:

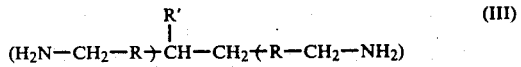
(III)

wherein R and R' are as defined hereinabove. The catalytic hydrogenation of an unsaturated dinitrile reactant of formula (II) results primarily in the formation of saturated diamine reaction products having the formula:

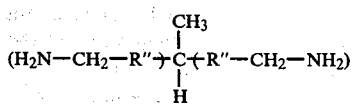

(IV)

wherein R" is as defined hereinbefore.

Materials that are considered to be suitable for employment in the production of the first catalyst component in the catalytic hydrogenation process of this invention include the oxides, halides, nitrates, sulfates, oxalates, acetates, carbamates, propionates, tartrates, hydroxides, and the like and mixtures thereof of palladium.

Materials that are considered to be suitable for employment in the production of the second catalyst component include the oxides, halides, nitrates, sulfates, oxalates, acetates, carbamates, propionates, tartrates, hydroxides, and the like, and mixtures thereof of nickel.

The alkali metal borohydrides suitable for reaction with the above-described palladium compounds and nickel compounds to produce the first and second components of the catalyst system of this invention include borohydrides of formula $MBH_4$ wherein M is lithium, sodium, potassium, rubidium or cesium. Sodium borohydride and potassium borohydride are especially preferred because of commercial availability.

The amount of sodium borohydride employed in reaction with the palladium compounds and nickel compounds can vary over a wide range depending, of course, on the reactivity of the unsaturated dinitrile and the desired degree of conversion of the unsaturated dinitrile to saturated diamine. Thus, a range of about 0.2 to 5, and preferably 0.5 to 2, moles of alkali metal borohydride per mole of total palladium compound and nickel compound can be employed in the practice of this invention, though it will be recognized that equimolar quantities of alkali metal borohydride and total palladium and nickel compounds are especially preferred.

The treatment of the nickel and palladium compounds with alkali metal borohydride can be conducted at any desired temperature. However, due to the exothermicity of the reaction, it is usually desirable to begin the treatment at room temperature and allow the reaction to proceed with or without external cooling. Allowing the reaction to proceed adiabatically from room temperature generates temperatures in the range of 150° to 200° C.

The mole ratio of the total metal of the first component (palladium) to the total metal of the second component (nickel) in mixtures thereof will generally be in the range of about 3/1 to about ⅓, preferably in the range of about 2/1 to about ½ and most preferably about 1/1. The weight ratio of catalyst to unsaturated dinitrile reactant, based on the weight of the total of first and second component metals contained therein for the one-step process and based on the weight of the individual catalyst components in each stage of the two-step process, can be varied as desired. For the purpose of maintaining reasonable reaction rates under economically attractive catalytic reaction kinetics, it is generally preferred that the weight ratio of the catalyst component metals to the unsaturated dinitrile reactants be maintained within a range of about 0.01:100 to about 30:100, and preferably in the range of about 0.1:100 to about 20:100.

One skilled in the art, in possession of this disclosure having studied the same, can determine by mere routine testing what will be for his particular circumstances the optimum parameters, said person having been given the foregoing and following information to as fully comply with the statute, rules and practice thereunder, yet to maintain some reasonable scope of presentation of what is now considered to be the best mode of carrying out the invention.

In the practice of this invention it is often desirable to employ catalytic amounts of the palladium component of the catalyst and the nickel component of the catalyst supported by a solid catalyst carrier which does not deleteriously affect the catalytic hydrogenation process of this invention. Such supports include, for example, carbon, kieselguhr, silica, alumina, silica-alumina, calcium carbonate, clays, and the like, and mixtures thereof.

The catalyst components of this invention are prepared by treating aqueous solutions or suspensions of the above-described palladium and nickel compounds with an aqueous solution of alkali metal borohydride. When no solid catalyst support is employed, the treatment of the palladium compounds and nickel compounds with alkali metal borohydride gives solid water-insoluble materials which demonstrates the catalytic activity of this invention. When a solid catalyst support is employed the support is suspended in an aqueous system also containing either the palladium or nickel compounds, which suspension is then either treated directly with the alkali metal borohydride solution, followed by separation of phases or, alternatively, is stripped of volatiles, re-suspended in water and then treated with alkali metal borohydride solution, followed by separation of solid and liquid phases and drying of the resultant solid supported catalyst. Thus, the palladium and nickel components of the catalyst of this invention are prepared independently of each other.

The palladium and nickel components of the inventive catalyst system can be combined with each other in several ways for use in a one-step hydrogenation process. The suspensions resulting from treatment of the individual palladium compounds and nickel compounds with alkali metal borohydride in the presence or absence of catalyst support can be mixed with each other before separation of the solid phase from the liquid phase and subsequent drying. Alternatively the solid catalyst components prepared in the presence or absence of solid support can be separated from their respective supernatent liquids and combined with each other either before or after a final drying step. Further alternatively, the palladium and nickel catalyst components after their independent preparations and subsequent recovery and drying steps, can be stored separately and ultimately mixed in the hydrogenation reactor.

When a support is employed the total of palladium or nickel (calculated as the metal) will generally be in the range of about 0.5 to about 50 wt. %, preferably in the range of about 1 to about 20 wt. %, based on the total weight of catalyst components and support.

Any hydrogenation temperature can be employed which provides the desired degree of catalytic efficiency in the hydrogenation of the branched-chain unsaturated aliphatic dinitrile-containing feedstock. The hydrogenation temperatures will generally be within the range of about 50° C. to about 200° C., preferably within the range of about 75° C. to about 150° C.

The catalytic hydrogenation of branched-chain unsaturated aliphatic dinitriles can be carried out at any hydrogen pressure wherein both the olefinic unsaturation and the nitrile groups are reduced in the presence of ammonia, hydrogen, and a suitable diluent. Generally, suitable hydrogen pressures are within the range of from about 500 to about 5,000 psia (3500 to 35,000 kPa), but lower or even higher hydrogen pressures can be employed. Preferably, due to economic considerations, hydrogen pressures within the range of about 600 to about 2,000 psia (4100 to about 13,600 kPa) are employed.

Any time interval suited for the catalytic hydrogenation of branched-chain unsaturated aliphatic dinitriles can be employed in the practice of this invention. However, time intervals economically attractive to the process are generally within the range of about 15 minutes to 5 hours for a batch hydrogenation process. A reaction time in the range of about 30 minutes to about 3 hours is sufficient and is presently preferred in order to ensure substantially complete hydrogenation of any unsaturated olefinic bonds and nitrile groups in the feedstock. Of course, it is recognized that reaction temperature, pressure and time are interrelated such that, for example, lower reaction temperatures frequently require higher hydrogen pressures and/or longer contact times to achieve substantially complete reduction.

The diluent utilized in the hydrogenation process of the present invention is a mixture of water and t-butanol containing from about 35 to about 65 percent by volume water based on total water plus t-butanol. To facilitate handling of the reaction mixtures, the weight ratio of unsaturated dinitrile reactants to diluent charged to the reaction zone is generally within the weight ratio range of about 0.1/100 to about 75/100, and is preferably in the range of about 5/100 to about 50/100.

Ammonia is employed in the process of this invention as a means of suppressing undesirable side reactions such as the formation of secondary and tertiary amines. Any amount of ammonia can be employed which is effective in deterring or reducing undesirable side reactions. In general, the mole ratio of ammonia to nitrile group will be in the range of about 1/1 to about 25/1 and preferably in the range of about 2/1 to about 10/1. The ammonia can be added to the hydrogenation process as liquid ammonia or as ammonium hydroxide. When ammonium hydroxide is employed the water portion thereof (considering ammonium hydroxide to be a solution of ammonia in water) is considered as part of the above-described diluent.

In two-step hydrogenation processes according to this invention the olefinic unsaturation is predominantly hydrogenated in the step employing the palladium catalyst component and the nitrile unsaturation is predominantly hydrogenated in the step employing the nickel catalyst component. The order of the steps is not believed to be critical to this invention. Thus either the nickel component or the palladium component can be employed first in the process. For best results ammonia is necessary to suppress the secondary amine formation in the step employing the nickel component, but is optional in the step employing the palladium component.

Recovery of the desired end product, the branched, saturated aliphatic diamines, as well as any resulting reaction by-products, unconsumed reactants, ammonia, hydrogen, and/or diluents can be carried out by any convenient separation means. In general, at the conclusion of the catalytic hydrogenation process, the reaction zone effluent is cooled and depressurized with the recovery, if desired, of any ammonia or diluent which is vented from the reaction zone effluent during the depressurization operation. The ammonia or diluent can be returned or recycled to the hydrogenation zone if desired. The reaction products can be separated from the catalyst by conventional filtration means. The filtrate containing the desired branched saturated diamines can be conveniently separated from any reaction by-products or any remaining diluent by any convenient fractional distillation.

EXAMPLE I

The following inventive and comparative runs demonstrate the hydrogenation efficiency obtained in a one-step hydrogenation process with an inventive catalyst (nickel component and palladium component) compared to the nickel or palladium components alone or the nickel component in combination with other noble metal catalyst components.

The catalyst components of this example were prepared by placing in a glass reactor at room temperature under a nitrogen atmosphere 120 ml of a 0.1 molar solution of the appropriate metal salt in water and adding thereto slowly with stirring 120 ml of a 0.1 molar solution of sodium borohydride in water. After the addition of sodium borohydride was complete, the resultant solid was removed by filtration, washed several times with water, and either dried under vacuum at 40°–50° C. or by aspiration at room temperature.

A 300 cc autoclave reactor was charged with 20 ml of the purified reaction product of 2 moles of acrylonitrile with 1 mole of isobutylene. This reaction product consisted essentially of a mixture of isomeric unsaturated dinitriles having 1 carbon-carbon double bond and 10 carbon atoms per molecule. The principle isomers were 5-methylenenonanedinitrile and 5-methyl-4-nonenedinitrile with very small amounts of more highly branched isomers such as 2-methyl-4-methyleneoctanedinitrile, among others. For simplicity, the above-described reaction product will hereafter be called diadduct (DA). Also charged to the autoclave was 50 ml t-butanol, 50 ml water, and the entirety of the above-described isolated solid catalyst component (0.012 mol theoretical). The system was flushed with nitrogen and charged with 15 gms ammonia. The reactor was pressured with hydrogen to the value given in Table I and heat was applied. As the hydrogen pressure decreased to the value given in Table I (as final pressure) the reactor was repressured and reaction continued for the additional specified time period. The mixture was stirred through the reaction period. The reactor was cooled, vented, and the contents filtered to remove the catalyst. The filtrate was condensed by removal of excess diluent on a rotary evaporator. Analysis of the residue by vapor-phase chromatography gave the results listed in Table I.

TABLE I

| | | HYDROGENATION | | | | | | | |
|---|---|---|---|---|---|---|---|---|---|
| | | Time | Pressure, psig[c] | | Temp.[d] | | Product[e] | | |
| Run No. | Metal Salt[a] | Min.[b] | Initial | Final | °C. | DA | UDA[g] | MND[h] | Other[i] |
| 1(inv.) | Ni(O$_2$CCH$_3$)$_2$ . 4H$_2$O | 22 | 1325 | 600 | 95 | | | | |

TABLE I-continued

| Run No. | Metal Salt[a] | Time Min.[b] | Pressure, psig[c] Initial | Pressure, psig[c] Final | Temp.[d] °C. | Product[e] DA | Product[e] UDA[g] | Product[e] MND[h] | Product[e] Other[i] |
|---|---|---|---|---|---|---|---|---|---|
|  | Pd(NO$_3$)$_2$ . 2H$_2$O | 94 | 1350 | 1375 | 150 | 0 | 0 | 96.3 | 2.9 |
| 2(Comp.) | Ni(O$_2$CCH$_3$)$_2$ . 4H$_2$O | 27 | 1275 | 900 | 120 |  |  |  |  |
|  | RuCl$_3$ . 1-3 H$_2$O | 99 | 1275 | 1150 | 160 | 0 | 27.4 | 66.2 |  |
| 3(Comp.) | Ni(O$_2$CCH$_3$)$_2$ . 4H$_2$O | 16 | 1225 | 900 | 57 |  |  |  |  |
|  | Rh(NO$_3$)$_3$ . 2H$_2$O | 127 | 1225 | 1225 | 147 | 0 | 26.0 | 70.6 |  |
| 4(Comp.) | Ni(O$_2$CCH$_3$)$_2$ . 4H$_2$O | 28 | 1300 | 775 | 67 |  |  |  |  |
|  | CoCl$_2$ | 70 | 1300 | 1400 | 155 | 0 | 38.4 | 59.7 |  |
| 5(Comp.) | Ni(O$_2$CCH$_3$)$_2$ . 4H$_2$O[j] | 127 | 1500 | 1300 | 175 | 0.3 | 26.4 | 68.0 |  |
| 6(Comp.) | Pd(NO$_3$)$_2$ . 2H$_2$O[j] | 17 | 1200 | 900 | 50 |  |  |  |  |
|  |  | 19 | 1200 | 750 | 150 |  |  |  |  |
|  |  | 20 | 1200 | 1100 | 150 | 70.2 | 22.5 | 2.3 |  |

[a]Metal salts employed in catalyst preparation. The two salts listed in runs 1 to 4 were treated independently with NaBH$_4$ then the reaction products were combined in the hydrogenation reactor.
[b]The first time listed is reaction time to first repressurization except Run 5 which is total reaction time. Subsequent times are not cumulative but represent time elapsed from repressurization to termination or to repressurization (Run 6).
[c]The first "final" pressure is the pressure prior to first repressurization. Subsequent "initial" and "final" values are repressurized value and value at termination.
[d]Maximum temperature reached during time period.
[e]Weight percent of reaction product mixture from glc analysis. Failure of values to total 100% may be attributed to heavy by-products not eluting from gas chromatograph or to inherent inaccuracies in measurement procedures.
[f]Diadduct, i.e., unreacted starting material.
[g]Unsaturated diamine. Partially hydrogenated starting material in which all nitrile groups are converted to primary amine group, but olefinic unsaturation is not completely hydrogenated.
[h]Fully hydrogenated product of which 5-methylnonanediamine is major component.
[i]Observed by glc but unidentified.
[j]Double batch of catalyst was employed to provide same total amount of catalyst component as in runs 1 to 4 (0.024 moles).

The data recorded in Table I demonstrate that neither the nickel salt/sodium borohydride reaction product nor the palladium salt/sodium borohydride reaction product are effective, alone, in obtaining complete hydrogenation of the starting material (runs 5 and 6). Comparative runs 2, 3, and 4 demonstrate that the nickel reaction product in combination with either ruthenium, rhodium, or cobalt reaction products is likewise not effective in obtaining complete hydrogenation. In inventive run 1 a much greater degree of hydrogenation (in fact, complete hydrogenation within the limits of the detection method) was obtained employing the combination of nickel salt/sodium borohydride reaction product and palladium salt/sodium borohydride reaction product compared to the comparative runs.

EXAMPLE II

In the following inventive runs employing a one-step hydrogenation process the scope of the invention is demonstrated by employing nickel salt/sodium borohydride reaction product and palladium salt/sodium borohydride reaction product in various proportions.

The following inventive runs 7, 8 and 9 were carried out as described for inventive run 1 above, except that, in the catalyst component preparation, proportions other than 1/1 nickel/palladium molar ratio were employed. The parameters and results are recorded in Table II.

TABLE II

| Run No. | Metal Salt, Mole[a] NiX | Metal Salt, Mole[a] PdX | Metal Salt, Mole[a] Ni/Pd | Hydrogenation[b] Time, Min. | Hydrogenation[b] Press., psig Initial | Hydrogenation[b] Press., psig Final | Hydrogenation[b] Temp., °C. | Product[b] DA | Product[b] UDA | Product[b] MND | Product[b] Other |
|---|---|---|---|---|---|---|---|---|---|---|---|
| 1 | 0.012 | 0.012 | 1/1 | 22 | 1325 | 600 | 95 |  |  |  |  |
|  |  |  |  | 94 | 1350 | 1375 | 150 | 0 | 0 | 96.3 | 2.9 |
| 7 | 0.018 | 0.006 | 3/1 | 25 | 1300 | 725 | 77 |  |  |  |  |
|  |  |  |  | 61 | 1375 | 1300 | 148 | 0 | 0 | 87.9 | 9.0 |
| 8 | 0.009 | 0.015 | 3/5 | 16 | 1225 | 600 | 55 |  |  |  |  |
|  |  |  |  | 38 | 1250 | 1000 | 115 |  |  |  |  |
|  |  |  |  | 15 | 1275 | 1200 | 117 | 0 | 2.4 | 94.5 |  |
| 9 | 0.006 | 0.018 | 1/3 | 20 | 1200 | 725 | 66 |  |  |  |  |
|  |  |  |  | 57 | 1275 | 1225 | 140 | 0 | 4.0 | 84.4 |  |

[a]NiX = Ni(O$_2$CCH$_3$)$_2$ . 4H$_2$O; PdX = Pd(NO$_3$)$_2$ . 2H$_2$O; Ni/Pd = molar ratio.
[b]All headings correspond to those in TABLE I.

The data in Table II show that all runs gave higher conversion of starting material to fully hydrogenated product than the comparative runs in Table I. They also show that a 1/1 molar ratio of Ni/Pd (run 1) gave a higher conversion to desired product than other ratios ranging from 3/1 to ⅓.

EXAMPLE III

The following inventive and comparative runs demonstrate the criticality of preparing the individual catalyst components independently prior to mixing thereof for a one-step hydrogenation process. Inventive run 10 also demonstrates the use of a solid catalyst support in the preparation of the individual catalyst components.

In inventive run 10 the individual catalyst components were prepared in the following manner. In a glass reactor, Ni(O$_2$CCH$_3$)$_2$.4H$_2$O (2.12 gm) was dissolved in 50 ml water and alumina (10 gm) was added, after which water was removed using a rotary evaporator. To the resultant solid was added slowly with stirring a solution of NaBH$_4$ (0.32 gm) in 50 ml water, after which the supernatant was decanted, the solid was washed thrice with water and the water was removed using a rotary evaporator. The palladium component for inventive run 10 was prepared in an analogous fashion to the nickel component. PdCl$_2$ (1.51 gm) was dissolved in 50 ml water and alumina (10 gm) was added, after which the water was removed. To the resultant solid was added slowly with stirring a solution of NaBH$_4$ (0.32 gm) in 50 ml water, after which the water was decanted, the solid washed thrice with the water and the water was stripped from the resulting solid.

For comparative run 11, the hydrogenation catalyst was prepared in the following manner. To a solution of Ni(O$_2$CCH$_3$)$_2$.4H$_2$O (2.12 gm) and PdCl$_2$ (1.51 gm) in 50 ml water was added alumina (10 gm) after which water was removed using a rotary evaporator. To the resultant solid was added with constant stirring a solution of NaBH$_4$ (0.64 gm) in 50 ml water, after which the solid was recovered, washed and dried.

For comparative run 12, the catalyst was prepared in the following manner. Alumina (20 gm) was added to a solution of Ni(O$_2$CCH$_3$)$_2$.4H$_2$O (4.24 gm) in 50 ml water, after which the water was removed by stripping. To the resultant solid was added with constant stirring a solution of NaBH$_4$ (0.64 gm) in 50 ml water after which the water was removed by stripping. The resultant solid was added to a solution of PdCl$_2$ (3.02 gm) in 50 ml water after which the water was stripped. To the resultant solid with constant stirring was added the solution of NaBH$_4$ (0.64 gm) in 50 ml water after which the solid was recovered, washed and dried.

For comparative run 13 the catalyst was prepared in the following manner. To a solution of Ni(O$_2$CCH$_3$)$_2$.4H$_2$O (2.12 gm) in 20 ml water a solution of NaBH$_4$ (0.32 gm) in 20 ml water was added dropwise. To a separate solution of PdCl$_2$ (1.51 gm) in 20 ml water was added dropwise with constant stirring a solution of NaBH$_4$ (0.32 gm) in 50 ml water. The two resultant suspensions were mixed together and alumina (20 gm) was added, after which the water was removed by stripping. The resultant non-homogeneous or inhomogeneous solid was manually separated into grayish-black alumina particles and black particles of material which did not contain alumina. The black particles were suspended in water and the discolored alumina was added after which the water was stripped. The resulting inhomogeneous solid was again manually separated into its components and the procedure was repeated several times until all of the precipitated metal-containing material had become associated with alumina particles.

The materials produced as described above were employed in the hydrogen action of the diadduct described in Example I. In each case, 10 gm of total supported catalyst (5 gm of each supported catalyst component in run 10) was placed in a 300 cc autoclave with t-butanol (50 ml), water [50 ml; in Run 10 50 ml NH$_4$OH (assumed to be 30% by weight NH$_3$) was used in place of water] and diadduct (20 ml). After flushing the reactor with nitrogen, ammonia was added (except Run 10 which already contained NH$_4$OH) and the reactor was pressurized with hydrogen and heated for the hydrogenation to proceed.

Reaction parameters and results are recorded in Table III.

TABLE III

| Run No. | Hydrogenation[a] | | | | Product[a] | | |
|---|---|---|---|---|---|---|---|
| | Time Min. | Press., psig Initial | Final | Temp., °C. | DA | UDA | MND |
| 10(Inv.)[b] | 52 | 1300 | 875 | 78 | | | |
| | 95 | 1275 | 1100 | 100 | 0 | 0.4 | 96.1 |
| 11(Comp.) | 45 | 1375 | 950 | 110 | | | |
| | 20 | 1425 | 1250 | 110 | 0 | 20.1 | 70.0 |
| 12(Comp.) | 118 | 1225 | 1200 | 105 | 0.7 | 15.3 | 79.9 |
| 13(Comp.) | 50 | 1175 | 975 | 77 | | | |
| | 85 | 1175 | 1175 | 97 | 38.6 | 32.3 | 18.5 |

[a]All headings correspond to those in TABLE I.
[b]In run 10 50 ml NH$_4$OH (30% by weight NH$_3$) was added instead of the 50 ml H$_2$O and 15 gm NH$_3$ added in runs 11, 12, and 13.

The data obtained in run 10 demonstrate that useful catalysts are obtained if the metal salt is placed on a solid support prior to reaction with the sodium borohydride. The data from comparative run 11 demonstrate that acceptable catalyst was not obtained if the nickel and palladium salts were mixed together prior to treatment with sodium borohydride. The data in comparative run 12 demonstrate that acceptable catalyst was not obtained if the nickel and palladium salts were treated with sodium borohydride sequentially on the same batch of catalyst suppport. The results of run 13 are not well understood, though it appears that, though the nickel and palladium salts were separately treated with sodium borohydride then mixed in suspension with alumina, during the workup and repeated manual separation of the inhomogeneous reaction product, the catalyst was somehow inactivated.

Thus, the data in the above working examples demonstrate that suitable catalysts for the hydrogenation of branched-chain unsaturated dinitriles in one-step processes are obtained by separate treatment of nickel compounds and palladium compounds with sodium borohydride in the presence or absence of solid support and subsequent combination thereof in accordance with the teachings of this invention.

EXAMPLE IV

The following inventive runs demonstrate the hydrogenation of unsaturated aliphatic dinitriles in a two-step process employing either the nickel catalyst component or the palladium catalyst component in the first step.

The nickel catalyst component was prepared by adding alumina (20 gm) to a solution of Ni(O$_2$CCH$_3$)$_2$.4H$_2$O (4.88 gm) in water (35 ml) after which the water was stripped. To the resultant solid was added slowly with stirring a solution of NaBH$_4$ (0.74 gm) in water (20 ml) after which the water phase was decanted and the solid was washed thrice with water and dried.

The palladium catalyst component was prepared in an analogous fashion by adding alumina (20 gm) to a solution of PdCl$_2$ (3.48 gm) in water (40 ml) followed by stripping of water. To the resultant solid was added slowly with stirring a solution of NaBH$_4$ (0.74 gm) in water (20 ml) after which the water phase was decanted and the solid was washed thrice with water and dried.

In the run 14A 5 of gm of the supported nickel catalyst component was placed in a 300 cc stirred autoclave with water (50 ml), t-butanol (50 ml) and diadduct (20 gm). After flushing with nitrogen, ammonia (15 gm) was added and the reactor was pressurized, heated, and repressurized as given in Table IV. The reactor was cooled and vented and the reaction product mixture was filtered and concentrated using a rotary evaporator. Analysis of the concentrate gave the results listed in Table IV.

In run 14B the concentrate from run 14A was placed in a 300 cc stirred autoclave reactor with 5 gm of supported palladium catalyst component, water (50 ml) and t-butanol (50 ml). After flushing with nitrogen, ammonia (15 gm) was added and the reactor was pressurized, heated and repressurized as given in Table IV. The reactor was cooled and vented and the reaction product mixture was filtered and concentrated using a rotary evaporator. Analysis of the final concentrated reaction product is given in Table IV.

Runs 15A and 15B were conducted as outlined for 14A and 14B except that the palladium component was employed in 15A and the nickel component was employed in 15B. Reaction parameters and results are given in Table IV.

TABLE IV

| Run No. | Catalyst Component | Hydrogenation[a] Time, Min. | Press., psig Initial | Final | Temp. °C. | Product[a] DA | UDA | SDN[b] | MND |
|---|---|---|---|---|---|---|---|---|---|
| 14A | Ni | 27 | 1375 | 975 | 62 | | | | |
| | | 80 | 1375 | 1350 | 90 | 0 | 84.4 | | 7.4 |
| 14B | Pd | 164 | 1150 | 1150 | 94 | 0 | 1.1 | | 93.5 |
| 15A | Pd | 160 | 1075 | 1000 | 100 | 0 | 3.4 | 89.6 | 6.5 |
| 15B | Ni | 17[c] | 1000 | 200 | 48 | | | | |
| | | 65 | 1250 | 1000 | 75 | 0 | 0 | | 98.7 |

[a]All headings except as noted correspond to those in TABLE I.
[b]SDN = saturated nitrile or saturated dinitrile.
[c]Run was interrupted by failure of a safety device which allowed depressurization. After repair and repressurization, run continued.

The data in Table IV demonstrate that two-step hydrogenation processes employing either of the catalyst components in the first step result in substantially complete hydrogenation of unsaturated dinitriles. The data also reveal that the nickel catalyst component is more active toward nitrile unsaturation while the palladium component is more active toward olefinic unsaturation.

In obtaining the data given herein it was determined that in the desired product all olefinic unsaturation was saturated and that all nitrile groups were converted to amine groups. In the concentrated reaction product mixture small amounts of unsaturated diamine and other unidentified by-products were sometimes obtained. Thus using a gas chromatographic analysis, in the MND portion of the product mixture, no compounds were eluted in the intervals corresponding to those of compounds having olefinic or nitrilic unsaturation. MND is known to contain no appreciable or recognizable olefinic or nitrilic unsaturation.

It now appears that the earlier described diluent, when one is employed, in the now preferred form of the invention, is best suited to carry out the invention. Other diluents which have been tried have yielded results which are inferior to those obtained using the earlier described diluent.

One skilled in the art in possession of this disclosure, having studied the same, may by testing determine other satisfactory diluents for carrying out the broader concepts of this invention.

Further, in the now preferred embodiment, an amines-formation suppressant, e.g., ammonia, is employed. One skilled in the art in possession of this disclosure, having studied the same, may determine other amines-formation suppressants. It now appears that primary, secondary and tertiary alkyl amines, such as methylamine, dimethylamine and triethylamine will be operative to suppress formation of presently undesired by-products.

Reasonable variation and modification are possible within the scope of the foregoing disclosure and the appended claims to the invention the essence of which is that there have been provided a process for the catalytic hydrogenation of a branched, unsaturated aliphatic dinitrile, to produce a branched, saturated aliphatic diamine, employing several catalytic components as a mixture in a one-step hydrogenation operation and sequentially in a two-step hydrogenation operation to obtain substantially complete hydrogenation, as described, of certain branched chain, unsaturated aliphatic dinitrile, also as described; that for the now preferred form of the invention a diluent, e.g., a water/t-butanol mixture, is employed and that in an also now preferred form of the invention an amines-formation suppressant, e.g., ammonia, is employed.

I claim:

1. A process for the catalytic hydrogenation of a branched, unsaturated aliphatic dinitrile which comprises subjecting the same under hydrogenation conditions to the presence of a catalytic material comprising a reaction product of an alkali metal borohydride with a palladium compound which is reducible by hydrogenation to the elemental form and a reaction product of an alkali metal borohydride with a nickel compound which is reducible by hydrogen to the elemental form.

2. A process according to claim 1 wherein the several components of catalytic material are in an admixture during a hydrogenation.

3. A process according to claim 1 wherein each of the catalytic components is separately used during a two-step hydrogenation process in which the compound or compounds to be hydrogenated are placed under hydrogenation conditions in the presence of each of the components sequentially.

4. A process according to claim 1 wherein the branched chain unsaturated aliphatic dinitrile is represented by the formula

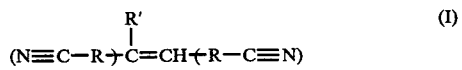

wherein each R is independently selected from an alkylene radical and an alkylidene radical and wherein R' is an alkyl radical.

5. A process according to claim 4 wherein R contains a number of carbon atoms in the range 1–15 and wherein the compound contains carbon atoms in the range 7–30 and R' has 1–6 carbon atoms.

6. A process according to claim 5 wherein the compound contains a number of carbon atoms in the range 8–16.

7. A process according to claim 5 wherein the compound contains a number of carbon atoms in the range 9-12.

8. A process according to claim 1 wherein the branched chain unsaturated aliphatic dinitrile is selected from the following:
4-methyl-3-hexenedinitrile,
4-ethyl-3-hexenedinitrile,
5-methyl-4-nonenedinitrile,
5-ethyl-4-decenedinitrile,
7-methyl-6-tridecenedinitrile,
7-methyl-6-pentadecenedinitrile,
12-methyl-12-tetracosenedinitrile,
10-hexyl-9-tetracosenedinitrile,
2,3-dimethyl-3-hexenedinitrile,
2,4,6-trimethyl-3-heptenedinitrile,
4-ethyl-6,7-dimethyl-3-octenedinitrile,
2,4,6-triethyl-3-octenedinitrile,
2-ethyl-4,6-dipropyl-3-octenedinitrile,
2-methyl-4,6,8,10-tetrapropyl-3-dodecenedinitrile,
2,4,7,9,11,13,15-heptaethyl-6-hexadecenedinitrile,
and the like and mixtures thereof.

9. A process according to claim 4 where in addition to the unsaturated dinitriles, there is present at least one unsaturated dinitrile having the formula

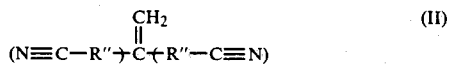

(II)

wherein each R" is independently selected from the following: an alkylene radical and an alkylidene radical, wherein each R" will have a number of carbon atoms in the range 1-15 and wherein the compound will contain a number of carbon atoms in the range 6-30.

10. A process according to claim 1 wherein the palladium component of the catalyst is produced employing an oxide, halide, nitrate, sulfate, oxalate, acetate, carbamate, propionate, tartrate, hydroxide of palladium and mixtures thereof.

11. A process according to claim 1 wherein the nickel component of the catalyst is produced employing an oxide, halide, nitrate, sulfate, oxalate, acetate, carbamate, propionate, tartrate, hydroxide of nickel, and mixtures thereof.

12. A process according to claim 1 wherein the alkali metal borohydride has the formula $MBH_4$ wherein M is selected from lithium, sodium, potassium, rubidium and cesium.

13. A process according to claim 1 wherein the alkali metal borohydride is at least one of sodium and potassium borohydrides.

14. A process according to claim 1 wherein the catalyst components are each of them separately prepared and then admixed.

15. A process according to claim 1 wherein the hydrogenation temperature is within approximate range of from about 50° C. to about 200° C. and the hydrogen pressure sufficient to hydrogenate both the olefinic unsaturation and the nitrile group is employed.

16. A process according to claim 1 wherein a reaction product of acrylonitrile, with isobutylene, essentially comprising a mixture of isomeric unsaturated dinitriles and including principally 5-methylenenonanedinitrile and 5-methyl-4-nonenedinitrile and relatively very small amounts of more highly branched isomers is subjected to hydrogenation.

17. A process according to claim 1 wherein the reaction is performed in the presence of a suitable diluent.

18. A process according to claim 17 wherein the diluent is a mixture of water and t-butanol.

19. A process according to claim 1 wherein an amines-formation suppressant is present.

20. A process according to claim 19 wherein the suppressant is ammonia.

* * * * *